United States Patent
Ciranni

(10) Patent No.: US 9,308,153 B2
(45) Date of Patent: Apr. 12, 2016

(54) METHOD FOR THE PREPARATION OF SURFACES OF DENTAL OR ORTHOPEDIC IMPLANTS

(71) Applicant: Cristiano Ugo Ciranni, Maranello (IT)

(72) Inventor: Cristiano Ugo Ciranni, Maranello (IT)

(73) Assignees: Cristiano Ugo Ciranni, Maranello (MO) (IT); Carlo Borrozzino, Medicina (BO) (IT); Furio Ruggeri, Bologna (IT)

( * ) Notice: Subject to any disclaimer, the term of this patent is extended or adjusted under 35 U.S.C. 154(b) by 0 days.

(21) Appl. No.: 14/485,825

(22) Filed: Sep. 15, 2014

(65) Prior Publication Data

US 2015/0076114 A1    Mar. 19, 2015

(30) Foreign Application Priority Data

Sep. 13, 2013   (IT) .............................. PR2013A0068

(51) Int. Cl.
| | | |
|---|---|---|
| *C03C 15/00* | (2006.01) | |
| *A61K 6/04* | (2006.01) | |
| *A61L 27/04* | (2006.01) | |
| *A61L 27/06* | (2006.01) | |
| *A61L 27/10* | (2006.01) | |
| *A61C 8/00* | (2006.01) | |
| *C23F 1/20* | (2006.01) | |
| *C23F 1/26* | (2006.01) | |
| *C23F 1/28* | (2006.01) | |
| *C23F 1/30* | (2006.01) | |

(52) U.S. Cl.
CPC ................ *A61K 6/04* (2013.01); *A61C 8/0093* (2013.01); *A61L 27/047* (2013.01); *A61L 27/06* (2013.01); *A61L 27/10* (2013.01); *C23F 1/20* (2013.01); *C23F 1/26* (2013.01); *C23F 1/28* (2013.01); *C23F 1/30* (2013.01); *A61L 2400/12* (2013.01); *A61L 2400/18* (2013.01)

(58) Field of Classification Search
CPC ............... C23F 1/02; C23F 1/26; C23F 1/28; C23F 1/30; A61C 2008/0046; A61K 6/04; A61L 27/047
USPC .................. 216/104; 623/23.5, 23.55, 23.38; 427/2.27
See application file for complete search history.

(56) References Cited

U.S. PATENT DOCUMENTS

| | | |
|---|---|---|
| 3,562,013 A | 2/1971 | Mickelson et al. |
| 5,571,188 A | 11/1996 | Ellingsen |
| 5,876,453 A | 3/1999 | Beaty |
| 6,689,170 B1 * | 2/2004 | Larsson et al. ............. 623/23.53 |
| 6,969,474 B2 | 11/2005 | Beaty |
| 7,501,073 B2 | 3/2009 | Wen et al. |
| 7,901,462 B2 | 3/2011 | Yang et al. |
| 8,221,499 B2 | 7/2012 | Lazzara |
| 8,221,639 B2 | 7/2012 | Towse et al. |
| 8,251,700 B2 | 8/2012 | Robb et al. |
| 8,632,843 B2 * | 1/2014 | Andersson et al. .......... 427/2.24 |
| 2003/0135282 A1 | 7/2003 | Anitua |
| 2004/0167632 A1 | 8/2004 | Wen et al. |
| 2008/0254201 A1 * | 10/2008 | Carinci et al. ............... 427/2.27 |

FOREIGN PATENT DOCUMENTS

| | | |
|---|---|---|
| EP | 1 449 544 | 8/2004 |
| EP | 1736182 | * 5/2006 |
| EP | 1 736 182 | 12/2006 |

OTHER PUBLICATIONS

Liao Juan et al. International Journal of Nanomedicine, (2010) pp. 261-267.*

Italian Search Report dated May 14, 2014, corresponding to the Foreign Priority Application No. PR2013A000068.

* cited by examiner

*Primary Examiner* — Duy Deo
*Assistant Examiner* — Maki Angadi
(74) *Attorney, Agent, or Firm* — Young & Thompson

(57) ABSTRACT

A method for the surface preparation of devices made of titanium or titanium alloys, zirconium, zirconia, alumina or zirconia/alumina compounds, stainless steels and cobalt-base superalloys for medical use; the devices being implantable in the human body or in animals and attached extracorporeal parts made with the same materials, particularly for dental and orthopedic implantology. The implantable device is treated by exposing at least one portion of the surface of the device to a solution including hydrofluoric acid, phosphoric acid, at least one surfactant substance and water; for a time period and in conditions sufficient to provide the surface of the implant with the desired surface roughness and the formation of self-induced surface titanium dioxide, maintaining the structural integrity of the device and without altering the centesimal measurement size. The surface thus is rinsed with demineralized water and ultrasounds in order to prevent metalosis phenomena.

10 Claims, No Drawings

METHOD FOR THE PREPARATION OF SURFACES OF DENTAL OR ORTHOPEDIC IMPLANTS

FIELD OF APPLICATION OF THE INVENTION

The present invention is inserted in the field of dental and orthopedic implantology, and specifically regards the preparation of surfaces of dental and/or orthopedic devices for human and animal use.

The implant is made of titanium or titanium alloys, zirconium, zirconia, alumina or zirconia/alumina compounds, stainless steels for medical use and cobalt-base superalloys for medical use.

In such a manner, it allow substituting the lost part, e.g. a tooth, in an optimal manner since it is biocompatible and particularly strong.

Once inserted in the bone, the part of the device that acts as a root, defined implant, is incorporated in the bone itself and must be capable of being integrated therewith, establishing a direct connection, not only at the functional level but also at the structural level, between the bone and the surface of the dental implant.

Indeed, an excellent osseointegration underlies the success of the dental and orthopedic implantology.

STATE OF THE ART

As said, the success of a device surgically implanted in living bone substantially depends on achieving and maintaining a durable bond between the surfaces in contact, i.e. the prosthesis and host bone.

It is generally known that the osseointegration of the implant made of titanium or titanium alloys, zirconium, zirconia, alumina or zirconia/alumina compounds, stainless steels for medical use and cobalt-base superalloys for medical use, also depends on the engraftment, i.e. diffusion, of the osteoblast cells on the surface of the orthopedic implant.

In addition, studies suggest that such cells will be more easily attachable to rough or porous surfaces, as compared to smooth surfaces.

Some examples of the prior art are described in the documents U.S. Pat. No. 7,901,462, US 20040167632, U.S. Pat. No. 5,571,188, U.S. Pat. No. 5,876,453, U.S. Pat. No. 6,969,474, U.S. Pat. No. 7,501,073, U.S. Pat. No. 8,221,499, U.S. Pat. No. 8,221,639, U.S. Pat. No. 8,251,700.

The aforesaid documents provide for the surface preparation of the implantable device, in a manner such to attack it with acid, usually hydrofluoric acid, so as to create a porous nano-surface and facilitate, as said, the engraftment.

The US20040167632 provides for obtaining a surface with nanometer roughness scale (in order to facilitate the growth of the bone tissue after the application of the implant) by means of:
  the exposure of at least one portion of the surface of said metal implant with a solution comprising
    at least one fluoride salt,
    at least one acid, (selected from among a group constituted by hydrochloric acid, nitric acid, sulfuric acid, acetic acid, lactic acid, perchloric acid, oxalic acid, tartaric acid, phosphoric acid, and mixtures thereof) and
    water.
The exposure occurs for a time period and in conditions sufficient to provide the implant with micron or nanometer scale surface roughness and neoformation of titanium oxide, considered optimal for osseointegration, maintaining the structural integrity of the implantable device.

After this, it provides for the cleaning of at least the portion of the treated surface and the metal elements exposed to the attack solution.

The drying of the implantable device thus follows.

Possibly, in addition to the above-indicated solution, the method also uses a sulfate salt.

The problem of the above-described method, and of the prior art in general, is underlined in two aspects:
  The first aspect regards the obtained optimal surface. It is necessary to be able to have an improved and controllable surface roughness and an improved formation of surface titanium dioxide;
  The second aspect regards the perfect cleaning at the end of the process. It is not sufficient to have a porous surface, rather it is also necessary that this is completely clean and lacks metal residues.

Exposition and Advantages of the Finding

A first object of the present finding discloses an improved method for the surface preparation of an implantable device, for dental or orthopedic use, obtained with a specific and precise mixture of acids and surfactants joined with a rigid application protocol. In such a manner, a device is obtained that is implantable in human or animal bone having a surface roughness in nanometer scale and self-induced surface oxide coating, in order to facilitate the acceptance and the growth of bone tissue or the apposition thereof, maintaining the structural integrity of the device.

A second object of the invention is to obtain a surface that is perfectly clean at the end of the described and claimed treatment.

The advantages are clear:
  The perfect surface preparation facilitates the engraftment of the bone tissue to the implant for dental or orthopedic use, once this is implanted in the host bone,
  The perfect surface cleaning prevents unfavorable metal parts or processing residues from coming into contact with the bone structure or with the adjacent tissues, preventing the phenomena of release of non-adhesive metals; in addition
  The perfect surface cleaning ensures improved operating conditions for the possible step of coating the same with antibacterial and antimicrobial substances, as well as a perfect joining thereof.
  The surface thus obtained, or at least part thereof can be immersed in antimicrobial and/or antibacterial substances, such as 99% pure colloidal silver; the covering is attached to the surface thus treated, without adhesives, ensuring the indicated properties.

Said objects and advantages are all achieved by the method for the surface preparation of implantable devices, for dental or orthopedic use, subject of the present finding, which is characterized by that provided in the below-reported claims.

DISCLOSURE OF THE INVENTION

The method provides for operating on a device, for medical use or orthopedic use, implantable in the human or animal bone, such as, but not limited to, dental or orthopedic prostheses.

The method is applied to implants made of titanium or titanium alloys, zirconium, zirconia, alumina or zirconia/alumina compounds, stainless steels for medical use and cobalt-base superalloys for medical use.

The method is applied to implants for medical or orthopedic use which may have undergone a previous treatment, such as sandblasting.

According to one embodiment, the method provides for the immersion of at least part of the implant for medical or orthopedic use in a solution comprising:
 a. hydrofluoric acid,
 b. phosphoric acid,
 c. at least one surfactant substance
 d. water.

The exposure occurs for a time period and in conditions sufficient to provide the surface of the implant with the desired surface roughness, and the induction of self-induced surface oxide, maintaining the structural integrity of the device.

The presence of both abovementioned acids in the solution induces in the surface the correct level of roughness and the formation of self-induced surface oxide (e.g. titanium oxide in the case of implants made of titanium), while the presence of the surfactants improves the wettability and the mixing of the other substances in the solution.

The immersion of at least portion of the implant in said solution occurs for an interval comprised between 2 and 10 minutes.

According to one embodiment, the method in addition provides for the application of ultrasonic washing, which are a fundamental part of the treatment.

The ultrasounds are applied at least at the end of the immersion in above-indicated water-acids-surfactants solution.

In the current case, after the exposure the following is provided in said solution:
 the immersion of at least part of the treated surface in bidistilled water
 the application of ultrasounds on said implant thus immersed; the ultrasounds are in the 22-35 KHz frequency range and are applied for a time interval comprised between five and ten minutes.

The aforesaid application of ultrasounds is repeated multiple times, rinsing the implant under running water at the end of each application.

The presence of the step of rinsing with bidistilled demineralized water allows removing titanium dioxide and other metals not perfectly adhered to the surface layer of the device, preventing metalosis phenomena.

According to a further embodiment, the method provides for completing with a rinsing in a solution comprising at least water and sodium bicarbonate.

After this, the subsequent drying is provided.

According to a further embodiment, the method provides for the application of the ultrasonic washing even before the already described immersion in the acid-water-surfactant solution, in order to remove processing residues or adhered dirt, above all in the threaded (hollow) internal parts of implantable devices adapted for coupling further extraosseous devices that act, for example, as an anchorage for dental prostheses.

Specifically, it provides for the immersion of at least the surface to be treated in distilled water and the application of ultrasounds on said implant thus immersed; said ultrasounds are in the 22-35 KHz frequency range.

According to a further embodiment it is provided, at the end of the drying step, to immerse at least part of the implant in a solution of 99.9% pure colloidal silver and in an interval comprised between 1000 and 10000 PPM, in nanoparticles with size less than 20 nanometers; the immersion occurring for less than 30 seconds.

There follows the drying of the implant immersed at a temperature less than 100° C.

The immersion of at least portion of the implant in said solution occurs for an interval comprised between 2 and 10 minutes.

According to one embodiment variant, the deposition of the silver can be carried out through a vacuum deposition method/implant (Physical Vapor Deposition).

Process Example

Take a device for dental or orthopedic use made of titanium or titanium alloys, zirconium, zirconia, alumina or zirconia/alumina compounds, stainless steels for medical use and cobalt-base superalloys for medical use, treated or non-treated with preceding systems such as sandblasting etc. . . .

Wash the implant in distilled water; the implant is placed inside a

Pyrex container and ultrasonic tank capable of emitting ultrasounds at 22-35 KHz frequencies.

A rinsing in running water is executed.

Introduce the solution in a Pyrex container containing a solution of hydrofluoric acid, phosphoric acid, at least one surfactant substance and water.

There is 5-10% phosphoric acid and 1-7% hydrofluoric acid. The implant is introduced into the solution, allowing it to interact therewith for 2 to 10 minutes.

Remove the implant and rinse under running water.

Fill a Pyrex container with bidistilled demineralized water and immerse at least the previously-treated portion with the solution.

Apply 22-35 kHz ultrasounds for 5 to 10 minutes.

The operation is repeated multiple times, rinsing with every operation.

Conclude with a rinsing in a solution of water and sodium bicarbonate.

Dry on a sterile ceramic plate.

Immerse the possible affected portion of the implant thus treated in a self-hygienizing solution of 99.9% pure colloidal silver in a percentage that ranges from 1000 PPM to 10000 PPM. The immersion occurs in a few seconds, preferably within thirty seconds.

Extract and dry at a temperature of max 100° C.

Analysis And Results

The implant treated according to the above-reported process example was the object of a testing method according to UNI EN ISO 10993-5:2009 and 1S010993-12:2012.

Description of the testing method: the cells are made to grow on plates up to the obtainment of a nearly confluent single layer. For each sample, three cell culture plates are prepared. In addition, three plates are prepared for the negative control, three for the positive control and three for the control of the extraction liquid. In the plates to be treated with the sample, the medium is sucked and substituted with the extract of the sample. The cell cultures are microscopically examined after 24 and 48 hours of incubation with the extract and the possible presence of cytotoxic effects produced by the sample extract is evaluated.

Results obtained: after qualitative evaluation, by means of microscopic examination of the cells after 24 and 48 hours of incubation, no considerable deviation emerged with respect to the indicated normal morphology.

The invention claimed is:
1. A method for the surface preparation of dental or orthopedic implants, comprising:

a) exposing at least one portion of said surface in an acid-water-surfactant solution, for a period of from 2 to 10 minutes to self-induce surface oxide, said solution comprising:
  i) hydrofluoric acid,
  ii) phosphoric acid,
  iii) at least one surfactant, and
  iv) water;
b) immersing the surface in bidistilled water and applying ultrasound to said immersed surface, said ultrasound being in the 22-35 kHz frequency range and applied for 5 to 10 minutes;
c) rinsing the implant under running water at an end of the ultrasound application;
d) repeating the step b) multiple times and rinsing with every operation;
e) completing with a rinsing in a solution comprising at least water and sodium bicarbonate; and
f) drying the surface.

2. The method according to claim 1, wherein said phosphoric acid in the solution is in a percentage comprised between five and ten percent.

3. The method according to claim 1, wherein said hydrofluoric acid in the solution is in a percentage comprised between one and seven percent.

4. The method according to claim 1, wherein the surface is made of titanium, or titanium alloys, zirconium, zirconia, alumina or zirconia/alumina compounds, stainless steels for medical use or cobalt-base superalloys for medical use, the method being adapted to endow the surface of said implant with nanometer roughness in order to facilitate the growth of the bone tissue after the application of the implant.

5. A method for the surface preparation of dental or orthopedic implants, comprising:
  a) exposing at least one portion of said surface in an acid-water-surfactant solution, to self-induce surface oxide, said solution comprising:
    i) hydrofluoric acid,
    ii) phosphoric acid,
    iii) at least one surfactant, and
    iv) water;
  b) immersing the surface in bidistilled water and applying ultrasound to said immersed surface, said ultrasound being in the 22-35 kHz frequency range and applied for 5 to 10 minutes;
  c) rinsing the implant under running water at an end of the ultrasound application;
  d) repeating the step b) multiple times and rinsing with every operation;
  e) completing with a rinsing in a solution comprising at least water and sodium bicarbonate;
  f) drying the surface;
  g) immersing a portion of the treated surface in a self-hygienizing solution of 99.9% pure colloidal silver; the silver is in a percentage that ranges from 1000 PPM to 10000 PPM; and
  h) extracting and drying at a temperature of max 100° C.

6. The method according to claim 5, wherein said immersing in step g) occurs for less than 30 seconds.

7. The method according to claim 5, wherein the surface is made of titanium, or titanium alloys, zirconium, zirconia, alumina or zirconia/alumina compounds, stainless steels for medical use or cobalt-base superalloys for medical use, the method being adapted to endow the surface of said implant with nanometer roughness in order to facilitate the growth of the bone tissue after the application of the implant.

8. The method according to claim 5, wherein the exposing in step a) is from 2 to 10 minutes.

9. The method according to claim 5, wherein said phosphoric acid in the solution is in a percentage comprised between five and ten percent.

10. The method according to claim 5, wherein said hydrofluoric acid in the solution is in a percentage comprised between one and seven percent.

\* \* \* \* \*